United States Patent

Suzuki et al.

[11] Patent Number: 4,822,516
[45] Date of Patent: Apr. 18, 1989

[54] DETERGENT COMPOSITION FOR CLOTHING INCORPORATING A CELLULASE

[75] Inventors: Akira Suzuki; Susumu Ito, both of Utsunomiya; Kikuhiko Okamoto, Koshigaya; Eiichi Hoshino; Michio Yokosuka, both of Utsunomiya; Moriyasu Murata, Chiba, all of Japan

[73] Assignee: Kao Corporation, Tokyo, Japan

[21] Appl. No.: 127,418

[22] Filed: Dec. 2, 1987

[30] Foreign Application Priority Data

Dec. 8, 1986 [JP] Japan .................. 61-292158

[51] Int. Cl.⁴ .................. C11D 7/42; C11D 3/386
[52] U.S. Cl. .................. 252/174.12; 252/DIG. 12; 435/188
[58] Field of Search .................. 252/174.12, DIG. 12; 435/188

[56] References Cited

U.S. PATENT DOCUMENTS 4,443,355 4/1984 Murata ..................... 252/174.12
4,648,979 3/1987 Parslow ..................... 252/8.8

FOREIGN PATENT DOCUMENTS 3207825 9/1982 Fed. Rep. of Germany.

Primary Examiner—Paul Lieberman
Assistant Examiner—Kathleen Markowski
Attorney, Agent, or Firm—Oblon, Fisher, Spivak, McClelland & Maier

[57] ABSTRACT

A novel detergent composition for clothing comprises a cellulase having a non-degrading index of the following equation of not less than 500

$$\text{non-degrading index} = \frac{\text{hydrolytic rate for low-crystalline cellulose}}{\text{hydrolytic rate for highly crystalline cellulose}}$$

The composition can not only remove the dirt in clothing articles without damaging them but also show the effect of mitigating the roughness of cloth to the touch and the effect of preventing decoloration.

1 Claim, 3 Drawing Sheets

FIG. 3

DETERGENT COMPOSITION FOR CLOTHING INCORPORATING A CELLULASE

BACKGROUND OF THE INVENTION

1. Field of the Invention

This invention relates to detergent compositions for clothing and more particularly, to clothing detergent compositions comprising a cellulase which has a good dirt-removing action and a good non-degrading property for insoluble celluloses including cotton.

2. Description of the Prior Art

In the field of clothing detergents, it is known that detergent compositions comprising cellulases are effective in removing dirt when used to wash clothing articles containing cellulosic fibers such a cotton and regenerated cellulose fibers (Japanese Patent Publication No. 59-49279) and are also effective in mitigating roughness by washing of clothes to the touch (Japanese Patent Application Laid-open No. 57-23699).

Since an aqueous solution of a detergent for clothing dissolved in water is neutral to alkaline in nature and is usually weakly alkaline, the cellulase used for this purpose is favorably an alkalophilic cellulase. Although applications of such a cellulase to detergents for clothing are not so popular, only several instances are known such as described, for example, in Japanese Patent Application Laid-open No. 57-145199.

Cellulase is a generic term for enzymes which act on cellulose and its derivatives and hydrolyze them into glucose, cellobiose, cellooligosaccharide. It has been called in various names depending upon the working mechanism, but the true nature of the cellulase has not been known yet. In this connection, however, the cellulase having the effect of removing dirt (Japanese Patent Publication No. 59-49279) and the cellulase having the effect of mitigating the roughness to the touch (Japanese Patent Application Laid-open No. 57-23699) are considered to have substantially different working mechanisms from each other.

In view of the differences in working mechanism among cellulases, when cellulases are acted on fibers made of cellulose and cellulose derivatives, various effects may be expected including removal of dirt such as soil, mitigation of roughness to the touch, prevention of fading (decoloration) of colored clothing articles and the like. Instead, there is the fear that cellulose and cellulose derivative fibers may be damaged. Especially, in home washing using a washing machine with a strong mechanical force, a serious problem of mechanical damages in fact arise. If the cellulose fibers are damaged with cellulases, the above problem will become more serious.

When attention is given to effective utilization of cellulose as a carbon resource, i.e. when solid cellulose is saccharified and the resultant product is used as a carbon source for alcohol fermentation, a cellulase having good capability of saccharification of solid cellulose is necessary. This type of cellulase exhibits the capability of saccharification against cotton. Accordingly, when the cellulase is applied to a detergent for clothing, there is the danger that the cotton suffers damages or degradation.

Only one alkali-resistant cellulase which is currently available for detergent purposes is Celluzyme 2400T, commercially sold from Novo Industry (Japanese Patent Application Laid-open No. 57-23699). This cellulase has fairly good dirt-removing effect but is inferior from the viewpoint of damage-suppressing property of cotton.

Accordingly, there is a demand for the development of a cellulase which does not damage and degrade clothing articles of cellulose fibers such as cotton, rayon, hemp and the like and mixed fibers thereof when used in neutral to alkaline, especially, weakly alkaline, clothing detergents and which has a satisfactory dirt-removing effect, and also of clothing detergent compositions comprising such a cellulose.

SUMMARY OF THE INVENTION

The present invention made studies on the mechanism of removing soil from clothing articles by the action of detergents. As a result, it was found that the reason why soil firmly deposited in cotton or other cellulose fibers cannot be adequately washed away by domestic washing is that the soil is trapped as layers in non-crystalline regions in the inside of cotton single fibers (cellulose). Known detergent ingredients such as surface active agents, builders, proteases and the like are unlikely to act on the trapped soil. It was also found that a certain kind of cellulase can infiltrate into the inside of cellulose fibers and that substantial differences are found among cellulases with respect to the activity on insoluble cellulose. In addition, the crystallinity of insoluble cellulose was found to have an inverse relation to the reactivity of cellulase. It was also found that when a cellulase having a low activity on highly crystalline cellulose and a high activity on low-crystalline cellulose is formulated in a detergent composition for clothing, the resulting composition exhibits good detergency with respect to cellulose clothing articles such as cotton and a low degree of damaging on the clothing articles. The present invention was accomplished based on the above findings.

According to the invention, there is provided a detergent composition for clothing which comprises a cellulase having a non-degrading index of the following equation of not less than 500

$$\text{non-degrading index} = \frac{\text{hydrolytic rate for low-crystalline cellulose}}{\text{hydrolytic rate for highly crystalline cellulose}}$$

DETAILED DESCRIPTION OF THE INVENTION AND PREFERRED EMBODIMENTS

The above non-degrading index is a ratio between hydrolytic rates for low-crystalline cellulose and highly crystalline cellulose. The respective hydrolytic rates can be obtained as follows: phosphoric acid-swollen cotton linters are provided as a low-crystalline cellulose substrate and cotton linters are used as a highly crystalline cellulose substrate; and the respective substrates are subjected to the enzymatic reaction and the resultant reducing sugar from each substrate is calculated as glucose.

More particularly, the non-degrading index is obtained by the following manner.

American raw cotton-derived cotton linters available from Daiwa Shizai Co., Ltd., are used as a highly crystalline cellulose sample and phosphoric acid-swollen cotton linters are used as a non-crystalline cellulose sample. The phosphoric acid-swollen cotton linters are prepared by the following procedure. Cotton linters are added portion by portion to an excessive amount of 85% phosphoric acid at 5° C. and sufficiently swollen and dissolved. Subsequently, the phosphoric acid solution of the cotton linters is dropped into an excess of acetone, thereby causing the cotton linters to precipitate. The acetone is replaced by fresh acetone to completely wash away the phosphoric acid. And the acetone is replaced by deionized water. The water is removed by drying to obtain phosphoric acid-swollen cotton linters. The crystallinity index of the cotton linters if 91% when the crystallinity index of cotton (American raw cotton) and the phosphoric acid-swollen cotton linters are, respectively, 100% and 0%.

The hydrolytic rates are, respectively, determined by subjecting the respective cotton linters substrates to reaction with a cellulase and the amount of the resultant reducing sugar is calculated as glucose according to the PHBAH method. The PHBAH method is described below. (PHBAH Method)

2 ml of a CMC (Sunrose A01MC with a degree of substituent of 0.68, available from Sanyo Kokusaku Pulp Co., Ltd.) solution (pH 9.0) was placed in a 25 ml test tube with a ground stopper, to which 2 ml of an enzyme sample solution was added for reaction on a water bath of 40° C. for 20 minutes. Subsequently, 2 ml of a PHBAH color-developing solution is added, followed by reaction for 10 minutes by heating in boiling water. After cooling in water, the solution was subjected to measurement of an absorbance at 410 nm using water as a reference. Similarly, a blank test is effected and the difference between both tests is provided as a measurement. The amount of reducing sugar is determined from the calibration curve prepared by the use of glucose. It will be noted that the PHBAH color-developing solution is prepared by dissolving 1.5 g of PHBAH and 5 g of potassium sodium tartarate in 100 ml of a 2% sodium hydroxide aqueous solution.

Cellulases having a non-degrading index, determined by the procedure described above, of not less than 500 are alkalophilic cellulases which are produced by alkalophilic microorganisms Bacillus sp. KSM-635 (FERM BP 1485), Bacillus sp. KSM-521 (FERM BP 1507), Bacillus sp. KSM-522 (FERM BP 1512), Bacillus sp. KSM-580 (FERM BP 1511), Bacillus sp. KSM-534 (FERM BP 1508), Bacillus sp. KSM-539 (FERM BP 1509), Bacillus sp. KSM-577 (FERM BP 1510), Bacillus sp. KSM-588 (FERM BP 1513), Bacillus sp. KSM-597 (FERM BP 1514) and the like. Alternatively, such cellulases may also be found in fractions of alkalophilic cellulases produced by Bacillus sp. KSM-344 (FERM BP 1506) and KSM-425 (FERM BP 1505).

The enzymatic properties of the above cellulases are described. The preparation of alkaline cellulase K which is typical of these cellulases is first described. (Preparation of Alkaline Cellulase K)

The alkaline cellulase is prepared by inoculating and cultivating in suitable media the strain of Bacillus sp. KSM-635 or its variant having a higher titer of capability of producing the enzyme than the strain.

For the production by fermentation of alkaline cellulase K, a suitable medium is sterilized such as by heating and the strain of Bacillus sp. KSM-635 (FERM BP 1485) is inoculated in the medium, followed by shaking or aeration spinner cultivation oat 22° to 40° C., preferably from 26° to 37° C. for 1 to 4 days. Good results are obtained when the pH is adjusted to 8 to 11. Since the production-by-fermentation medium is alkaline in nature, it may sometimes be expanded, which will be solved by adding a suitable antifoamer in an appropriate manner.

The medium used for the production of the alkaline cellulase K should contain utilizable nitrogen sources and carbon sources in combination. These nutrient sources are not limited. For instance, nitrogen sources include inorganic sources ammonium nitrate, ammonium sulfate, ammonium chloride, ammonium phosphate, sodium nitrate and the like, and corn gluten meal, bean flour, corn steep liquor, casamino acid, yeast extract, Pharmamedia, sardine meal, meat extract, peptone, Hypro, Ajipower, corn soybean meal, coffee grounds, cotton seed oil meal, Cultivater, Amiflex, Ajipron, Zest, Ajix, and the like. Examples of the carbon sources include plant fibers such as chaff, bran, filter paper, ordinary papers, sawdust and the like, and waste molasses, invert sugar, CMC, Avicel, cellulosic cotton, xylan, pectin and the like. Further utilizable carbon sources include, for example, ribose, arabinose, xylose, glucose, mannose, fructose, maltose, sucrose, trehalose, mannitol, inositol, glycerin and the like, and organic acids such as acetic acid, citric acid and the like. Any media using combinations of these nitrogen and carbon sources may be used in the practice of the invention and the nutrient sources should not be limited to any specific ones. Aside from these ingredients, phosphoric acid and inorganic salts such as of $Mg^{2+}$, $Ca^{2+}$, $Mn^{2+}$, $Zn^{2+}$, $Co^{2+}$, $Na^+$, $K^+$ an and, if necessary, small amount of inorganic and organic nutrient sources may be suitably added to the medium.

The collection and purification of the intended alkaline cellulase K from the thus obtained culture product may be effected by any known techniques used for ordinary enzymes as will be particularly described in examples appearing hereinafter.

For instance, the culture product may be subjected to centrifugal separation or filtration to separate the bacillus cells therefrom. The thus obtained filtrate and cells are subjected to ordinary isolation methods including, for example, salting-out, isoelectric precipitation, solvent precipitation (using methanol, ethanol, isopropanol, or the like), thereby separating the protein as a precipitate. Alternatively, ultrafiltration (e.g. Diaflow Membrane YC, available from Amicon Co., Ltd.) may be used for concentration to obtain alkaline cellulase K. After precipitation in ammonium sulfate (30 to 70% saturated fraction) for the salting-out method or 75% ethanol for the solvent precipitation method, the enzyme may be filtered or centrifugally separated or desalted to obtain a freeze-dried powder. The desalting may be effected by an ordinary procedure such as dialysis or gel filtration using Sephadex G-25 or the like. Moreover, the purification of the enzyme is possible by a suitable combination of, for example, a hydroxy apatite chromatography, an ion exchange chromatography using DEAE-Sephadex or DEAE-cellulose, and a molecular sieve gel chromatography using Sephadex, Biogel or the like.

The thus obtained alkaline cellulose K has the following physical and chemical properties.

(1) Activity

The present enzyme has a Cx enzymatic activity of acting on CMC. However, it also acts on phosphoric acid-swollen cellulose. The present enzyme has Avicelase activity, that is enzyme activity which acts on crystalline cellulose (cellulosic cotton) and cellulose having high crystallinity (Avicel); $C_1$ enzyme activity typical of which is a filter paper-degrading activity (FPDase); and $\beta$-glucosidase activity which acts on cellobiose and cellooligosaccharide as an enzyme specificities. In addition, the enzyme slightly acts on the artificial substrate of p-nitrophenyl cellobioside to liberate p-nitrophenol.

(2) Substrate specificity

The alkaline cellulase K has not only the main activity of CMCase activity, but also activities of Avicelase, FPDase ($C_1$ activity) and a degradation activity on the artificial substrate of p-nitrophenyl cellobioside (Table 1).

TABLE 1

| Action of Enzyme | Specific Activity (Units/g of enzyme) |
| --- | --- |
| Beta-glucosidase | 0.7 |
| PNPCase* | 5.2 |
| CMCase | 298 |
| FPDase | 1.2 |
| Avicelase | 1.1 |

*p-nitrophenyl cellobioside degrading activity (3) Working pH and optimum pH

The working pH of the present enzyme is from 4 to 12 and the optimum pH is approximately from 9 to 10. At about a pH of 10.5, there appears a shoulder.

(4) pH stability

Stable pH values, which are determined by allowing the enzyme to stand in buffer solutions of differnt pH at 40° C. for 10 minutes and 30 minutes, are, respectively, from 4.5 to 10.5 and 6.8 to 10. Standing at 5° C. ensures the stability at pH of from 4 to 11 at least over 1 month.

(5) Working temperature range and optimum temperature

The present enzyme works in a wide temperature range of from 10° C. to 65° C. When the reaction is effected in a glycine buffer solution (pH 9) for 20 minutes, the optimum temperature is found to be about 40° C.

(6) Thermal stability

When thermally treated in a glycine buffer solution (pH 9) at different temperatures for 20 minutes, the present enzyme is not inactivated at all at about 40° C., and has a residual activity about 50% at 60° C. and about 25% at 70° C.

(7) Measuring methods of enzymatic activities (i) CMCase activity 0.1 ml of an enzyme solution was added to a substrate solution composed of 0.2 ml of CMC (2.5%), 0.1 ml of a 0.5M glycine buffer solution (pH 9.0) and 0.1 ml of deionized water, followed by reaction at 40° C. for 20 minutes. After completion of the reaction, reducing sugar was quantitatively determined by a 3,5-dinitrosalicyclic acid (DNS) method. More specifically, 1 ml of a DNS reagent was added to 0.5 ml of the reaction mixture and heated at 100° C. for 5 minutes for color development, followed by cooling and dilution with 4.5 ml of deionized water. This was subjected to colorimetry at an absorbance of 535 nm. The enzyme titer determined as one unit is an amount of the enzyme which is capable of producing 1 $\mu$mol of glucose in one minute under the above-described conditions.

(ii) Decomposition activity of PNPC

A suitable amount of CMCase was acted at 30° C. on 1.0 ml of a reaction solution containing 100 $\mu$mol of a phosphate buffer solution (pH 7.0) and 0.1 $\mu$mol of PNPC (Sigma Co., Ltd.), after which 0.3 ml of 1M $Na_2CO_3$ and 1.7 ml of deionized water were added in this order, followed by subjecting the resultant free p-nitrophenol to colorimetry at 400 nm. The amount of the enzyme capable of liberating 1 $\mu$mol of free p-nitrophenol in one minute under the above conditions was determined as one unit.

(iii) Avicelase and FPDase activities 2 ml of a reaction solution for measurement of the CMCase activity was provided, to which there was added, instead of the CMC substrate, 20 ml of Avicel (Merck & Co., Inc.) or a bulk piece of a filter paper having a width of 0.5 cm and a length of 5 cm (filter paper for determination of cellulase activity, Toyo No. 51-Specific), thereby determining Avidelase and FPDase activities. An amount of the enzyme capable of liberating 1 $\mu$mol of reducing sugar, calculated as glucose, in one minute under the above conditions was determined as one unit.

(iv) The quantitative determination of proteins was effected by the use of Bio-Rad Protein Assay Kit (Bio-Rad Laboratories) and bovine serum albumin was used for calculation as a standard protein.

(8) Influence of chelating agents

The resistant of an enzyme for detergents to chelating agents in a builder used as a reaction composition is the most important factor. The alkaline cellulase K was pretreated with EDTA (0.5 mM), EGTA (0.5 mM), NTA (0.5 mM), sodium tripolyphosphate (STPP, 50 mg/ml) and zeolite (5 mg/ml) and subjected to determination of a residual activity, but any influence were not recognized.

(9) Influence of proteinases

Proteinases function to improve the detergency of detergent compositions. Accordingly, it is a matter of course to further improve the detergency by adding cellulases to proteinase-containing detergents. For this purpose, it is necessary to satisfy the requirement that cellulases for detergents are not hydrolyzed by proteinase and can stably maintain the activity. Alkaline cellulase K has a good resistance to actually employed proteinases for detergents (e.g. API-21), Maxatase, Alkalase and the like) and ordinary proteinases (e.g. pronase) (Table 2).

TABLE 2

| Added Proteinase | Concentration (wt %) | Relative Residual Activity (%)* |
| --- | --- | --- |
| API-21 | 0.002 | 98 |
| (Showa Denko) | 0.02 | 100 |
| | 0.2 | 114 |
| Maxatase | 0.002 | 113 |
| (Gist) | 0.02 | 99 |
| | 0.2 | 99 |
| Alkalase | 0.002 | 110 |
| (Novo) | 0.02 | 108 |
| | 0.2 | 99 |
| Pronase | 0.002 | 99 |
| (Sigma) | 0.02 | 98 |

TABLE 2-continued

| Added Proteinase | Concentration (wt %) | Relative Residual Activity (%)* |
|---|---|---|
| | 0.2 | 102 |

*Treated with the respective proteinases at 15° C. for 12 hours. The activity of an enzyme preparation not treated was taken as 100% and the activity of the respective treated preparations was indicated as an index to the non-treated preparation.

(10) Influence of metals

Divalent metal ions ($Hg^{2+}$, $Cu^{2+}$ and the like) at a suitable concentration given an effect of inhibition. A slight degree of inhibition is experiences by means of monoiodoacetic acid and p-chloromercuribenzoate.

(11) Influence of surface active agents

Alkaline cellulase K suffers little inhibition of activity by means of various surface active agents such as, for example, LAS, AS, ES, AOS, alpha-SFE, SAS, polyoxyethylene secondary alkyl ethers, fatty acid salts (sodium salts), and dimethyldialkylammonium chloride.

(12) Molecular weight (gel chromatography)

Having a maximum peak at 180,000±10,000.

The alkaline cellulases indicated in Table 3 have a non-degrading index not less than 500 and can be prepared in the same manner as alkaline cellulase K. The enzymatic properties of these enzymes indicated in the following table are also measured according to the measuring methods for alkaline cellulase K.

The methods for preparing these alkaline cellulases are disclosed in detail in the following patent applications: Japanese Patent Application Nos. 257776/1986, 257777/1986, 257778/1986, 283742/1986, 289812/1986, 16551/1987, 16552/1987, 16553/1987, 57644/1987, 67442/1987, 194140/1987, 194142/1987 and 194143/1987.

TABLE 3

| Alkaline Cellulase | K-344 | K-534 | K-539 | K-577 | K-425 | K-521 | K-580 |
|---|---|---|---|---|---|---|---|
| pH | | | | | | | |
| Working pH | 3–12.5 | 3–12.5 | 3–12.5 | 3–12 | 3.5–12.5 | 3–12.5 | 3–12.5 |
| 50% range | 4.5–11 | 4.5–10.5 | 4–11 | 4.5–10.5 | 5.5–10.5 | 4.5–10.5 | 4–10.5 |
| Optimum pH | 6 | 6.5 | 7 | 7 | 8–10 | 7–10 | 7–10 |
| pH Stability | 5–10 | 5–11 | 5–12 | 5–12 | 5–11 | 5–12 | 4.5–12 |
| 50% range | 4.5–12 | 4.5–12.5 | 3.5–12.5 | 4.5–12.5 | 3–12 | 4.5–12.5 | 3.5–12.5 |
| Temperature | | | | | | | |
| Working Temp. | 15–80 | 15–85 | 15–85 | 15–75 | 15–75 | 20–80 | 20–80 |
| 50% range | 40–75 | 45–75 | 45–75 | 40–65 | 35–55 | 45–65 | 50–75 |
| Optimum Temp. | 70 | 70 | 60 | 60 | 50 | 60 | 65 |
| Temp. Stability | 30 | 40 | 50 | 50 | 30 | 40 | 55 |
| 50% range | 55 | 65 | 60 | 55 | 50 | 55 | 65 |
| Molecular Weight (× 1000) | 16 | 15 30 | 18 29 | 17 30 | 35 | 31 | 18 50 |
| Influence of Metal | | | | | | | |
| Inhibition | $Hg^{2+}$ $Pb^{2+}$ | $Hg^{2+}$ | $Hg^{2+}$ | $Hg^{2+}$ | $Hg^{2+}$ $Ba^{2+}$ | $Hg^{2+}$ | $Hg^{2+}$ |
| Activation | $Co^{2+}$ | $Ba^{2+}$ | $Ba^{2+}$ $Ca^{2+}$ $Cd^{2+}$ | $Ba^{2+}$ $Ca^{2+}$ $Co^{2+},Cd^{2+}$ | $Co^{2+}$ | $Ca^{2+}$ | $Ba^{2+}$ $Ca^{2+}$ $Co^{2+},Cd^{2+}$ · |
| Influence of Protenase | No-deactivation | → | → | → | → | → | → |
| Influence of Surface Active Agent | a | b | b | a | a | b | b |
| Influence of SDS | b | b | a | a | a | a | b |
| Influence of Chelating Agent | a | b | b | a | b | a | a |
| Specificity of Substrate | | | | | | | |
| CMC | + | + | + | + | + | + | + |
| Cellulose Powder | + | + | + | + | + | + | + |
| Avicel | + | + | + | + | + | + | + |
| Filter Paper | + | + | + | + | + | + | + |
| PNPC | + | + | + | − | + | + | − |
| Celobiose | − | − | − | − | + | + | − |
| Microorganism Produced (Bacillus sp.) | KSM-344 | KSM-534 | KSM-539 | KSM-577 | KSM-425 | KSM-521 | KSM-580 |

| Alkaline Cellulase | K-588 | K-597 | K-522 | CMCase I | CMCase II | E-II | E-III |
|---|---|---|---|---|---|---|---|
| pH | | | | | | | |
| Working pH | 3–13 | 3–13 | 3–12.5 | 3.5–12.5 | 3–12 | 4–12.5 | 4–12.5 |
| 50% range | 4.5–10.5 | 4.5–11.5 | 4.5–10.5 | — | — | 5.5–11 | 6–10.5 |
| Optimum pH | 7 | 7 | 7–10 | 6–11.5 | 9.5 | 7–10 | 7–9 |
| pH Stability | 5–11.5 | 5–11.5 | 5–12 | 5–12 | 5–12 | 6–11 | 6–10 |
| 50% range | 4.5–12.5 | 4.5–12.5 | 4.5–12.5 | — | — | 5.5–11.5 | 5.7–11.5 |
| Temperature | | | | | | | |
| Working Temp. | 15–80 | 16–80 | 15–80 | 10–60 | 5–58 | 10–80 | 10–80 |
| 50% range | 45–65 | 45–75 | 45–65 | — | 15– | 30–65 | 30–62 |
| Optimum Temp. | 60 | 60 | 60 | 22–53 | 14–45 | 50 | 50 |
| Temp. Stability | 40 | 50 | 40 | — | 40 | 50 | 50 |
| 50% range | 55 | 55 | 55 | — | — | 55 | 55 |
| Molecular Weight (× 1000) | 27 30 | 40 | 35 | 145 | 17 | 61 | 61 |
| Influence of Metal | | | | | | | |

TABLE 3-continued

| | | | | | | | |
|---|---|---|---|---|---|---|---|
| Inhibition | $Hg^{2+}$ | $Hg^{2+}$ | $Hg^{2+}$ | $Hg^{2+}$ $Zn^{2+},Ni^{2+}$ $Co^{2+},Cu^{2+}$ | $Hg^{2+},Zn^{2+}$ $Co^{2+},Ni^{2+}$ $Ca^{2+},Cu^{2+}$ | $Hg^{2+}$ | $Hg^{2+}$ |
| Activation | $Fe^{2+}$ $Mn^{2+}$ | $Co^{2+}$ | | $Ba^{2+}$ $Mn^{2+}$ | $Mg^{2+},Mn^{2+}$ $Ca^{2+},Ba^{2+}$ $Fe^{2+},Li^{+}$ $K^{+},Na^{+}$ | $Co^{2+}$ | $Co^{2+}$ |
| Influence of Protenase | No-deactivation | → | → | → | → | → | → |
| Influence of Surface Active Agent | b | b | b | b | b | b | b |
| Influence of SDS | a | b | a | — | — | a | a |
| Influence of Chelating Agent | a | b | b | a | a | b | b |
| Specificity of Substrate | | | | | | | |
| CMC | + | + | + | + | + | + | + |
| Cellulose Powder | — | + | + | + | + | — | — |
| Avicel | — | + | + | + | + | — | — |
| Filter Paper | + | + | + | + | + | — | — |
| PNPC | + | + | + | + | + | — | — |
| Celobiose | — | — | — | + | + | — | — |
| Microorganism Produced (Bacillus sp.) | KSM-588 | KSM-597 | KSM-522 | KSM-635 | KSM-635 | KSM-522 | KSM-522 | a: no inhibition,
b: almost no inhibition

If these alkaline cellulases are not purified to a satisfactory extent, the non-degrading index may sometimes be below 500. For instance, when the alkaline cellulases K-344 and K-425 are prepared according to the preparation method for alkaline cellulase K, the non-degrading indices of these cellulases cannot exceed 500. However, these alkaline cellulases are further purified by utilizing the affinity chromatography described, for example in Japanese Patent Application Laid-open No. 62-62898, the resultant products exhibit a non-degrading index over 500.

It will be noted that when cellulase-producing bacilli other than the above alkaline cellulase-producing bacilli are varied and grown so as to enhance the productivity of cellulase whose non-degrading index is specifically over 500, these variants are also usable in the practice of the invention.

In the clothing detergent composition of the invention, a cellulase having a non-degrading index not less than 500 may be used, as an essentially ingredient, singly or in combination with other cellulase. Where combinations with other cellulases are used, the total of non-degrading indecies of the respective cellulases represented by the following equation should be not less than 500.

$$\text{Non-degrading index } (A) = \sum_{i=1}^{\eta} Xi \cdot Ai$$

(in which Xi is a fraction of CMCase of i component, and Ai is a non-degrading index of the i component.)

The detergent composition of the invention is prepared by formulating a cellulase or its fraction components satisfying the above requirement in known detergent ingredients. For this purpose, the cellulase is separated and collected from a fermentation broth by ordinary enzyme collection methods and, if necessary, fractionally purified. Further, the collected cellulase may be used in the form of a liquid, powder or granule depending on the manner of application. When the detergent composition is liquid, the cellulase used is preferably a liquid enzyme. For powdery or granular detergent compositions, the cellulase is preferably used as a granular enzyme. The granulation of the enzyme may be effected by ordinary enzyme granulation techniques, of which a coating method is preferred in view of the stability of enzyme and the safety in handling.

The content of a cellulase per kg of a detergent composition is preferably from 50 to 20,000 units as CMCase unit, more preferably from 250 to 10,000.

The present invention may be applied either to phosphate detergents containing phosphate builders or phosphate-free detergents not containing phosphate builders, or may also be applied to liquid, powder or granular detergents.

In the practice of the invention, known detergent ingredients used in combination with the cellulase or its fractional components are described below.

(1) Surface active agents

Anionic surface active agents such as linear alkylbenzenesulfonates whose alkyl group has from 10 to 16 carbon atoms on average, alkylethoxy sulfates which have a linear or branched alkyl group having from 10 to 20 carbon atoms on average and in which 0.5 to 8 moles, on average, of ethylene oxide are added in one molecule, alkylsulfate which has an alkyl group having 10 to 20 carbon atoms on average, olefinsulfonates having from 10 to 20 carbon atoms on average in one molecule, alkanesulfonates having from 10 to 20 carbon atoms on average in one molecule, methyl or ethyl ester salts of alpha-sulfofatty acids having from 10 to 20 carbon atoms on average in one molecule, higher fatty acid salts having from 8 to 20 carbon atoms on average and alkyl ether carboxylates which have a linear or branched alkyl group having from 10 to 20 carbon atoms and in which 0.5 to 8 moles, on average, of ethylene oxide are added in one molecule; nonionic surface active agents such as polyoxyethylene alkyl ethers which have an alkyl group having from 10 to 20 carbon atoms on average and in which 1 to 20 moles of ethylene oxide are added, higher fatty acid alkanolamides and alkylene oxide adducts thereof, and the like; and betaine-type amphoteric surface active agents, sulfonate-type amphoteric surface active agents, phosphate surface active agents, amino acid surface active agents, cationic surface active agents and the like.

The surface active agent is used in an amount of from 5 to 60 wt % (hereinafter referred to simply as %) of the detergent composition. Preferably, the surface active agent is added in an amount of from 10 to 45% for powder detergent compositions and from 20 to 55% for liquid detergent compositions.

(2) Divalent metal ion collectors

Condensed phosphates such as tripolyphosphates, pyrophosphates, orthophosphates and the like, aluminosilicates such as zeolite, nitrilotriacetates, ethylene diamine tetraacetates, citrates, isocitrates, polyacetal carboxylates, and the like.

The divalent metal ion collectors are formulated in an amount of from 0 to 50%, preferably from 5 to 40%. Favorably, phosphorus-free divalent metal ion collectors are used.

(3) Alkali agents and inorganic salts

Silicates, carbonates, sesqui-carbonates, sulfates and the like. These are formulated in an amount of from 0 to 80%.

(4) Re-contamination preventives

Polyethylene glycol, polyacrylates, polyacrylic acid copolymers, polyvinyl alcohol, polyvinylpyrrolidone, carboxymethyl cellulose and the like. The preventive is added in an amount of from 0 to 10%, preferably from 1 to 5%.

(5) Enzymes

Proteinases, amylases, lipases, hemicellulase, beta-glycosidase, glucose oxidase, cholesterol oxidase and the like.

(6) Collectors and reducing agents for effective chlorine in city water

The collectors for effective chlorine are ammonium sulfate, urea, guanidine hydrochloride, guanidine carbonate, guanidine sulfamate, thiourea dioxide, monoethanolamine, diethanolamine, triethanolamine; amino acids such as glycine, sodium glutamate and the like; proteins such as bovine serum alubmin, casein and the like; hydrolyzates of proteins; meat extract, fish extract, and the like.

The reducing agents include alkali metal and alkaline earth metal salts such as thiosulfates, sulfites, dithionites and the like, and Rongalite C.

(7) Bleaching agents

Percarbonates, perborates, hydrogen peroxide adducts of sodium sulfate or sodium chloride, zinc or aluminium salts of sulfonated phthalocyanine, and the like.

(8) Fluorescent dyes

Fluorescent dyes ordinarily used for clothing detergents.

(9) Solubilizing agents

The following solubilizing agents may be used for liquid detergents.

Lower alcohols such as ethanol; lower alkylbenzenesulfonates such as benezenesulfonates, p-toluenesulfonates and the like; polyols such as propylene glycol; and the like.

(10) Others

Aside from the above ingredients, perfumes, caking preventives, activators for enzyme, antioxidants, preservatives, dyes, bluing agents and the like ordinarily used for detergents may be used, if necessary.

When a detergent base used in the present invention is in the form of a powder, it may be one which is prepared by any known preparation methods including a spray-drying method and a granulation method. The detergent base obtained particularly by the spray-drying method and/or spray-drying-granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. The granules have a size of from 50 to 2000 micrometers. After the spray-drying, perfumes, enzymes, bleaching agents, inorganic alkaline builders such as zeolite and sodium carbonate may be added. With a highly dense, granular detergent base obtained such as by the spray-drying-granulation method, various ingredients may also be added after the preparation of the base.

When the detergent base is liquid, it may be either a homogeneous solution or a inhomogeneous dispersion.

The cellulase of the invention having a defined non-degrading index specifically acts on non-crystalline cellulose as compared with highly crystalline cellulose and decomposes it. Since the dirt in clothing articles is usually caught in non-crystalline cellulose regions which are formed highly crystalline cellulose which has undergone a change for some reasons, it can be removed by the use of detergent composition of the invention without damaging the clothing article. Moreover, the detergent comprising the cellulase shows various effects including not only the dirt-removing effect, but also the effect of mitigating the roughness of cloth to the touch and the effect of preventing decoloration.

The present invention is described in more detail by way of references and examples. The examples should not be construed as limiting the present invention.

Reference 1

(i) 1 g of a soil collected at Ichikai-machi, Haga-gun, Tochigi-ken, Japan was suspended in 10 ml of a sterilized physiological saline and thermally treated at 80° C. for 30 minutes. The thermally treated solution was suitably dilute and spread plated on a master plate (composed of 1% of a meat extract (Oxoid Co., Ltd.), 1% of a Bacto peptone (Difco Co., Ltd.) 1% of NaCl, 0.1 % of $KH_2PO_4$, 0.5% of $Na_2CO_3$ and 1.5% of Bacto agar-agar), followed by cultivation at 30° C. for 3 days, thereby forming colonies. Transplantation on a 2% CMC-containing master plate according to a replica method was conducted, followed by cultivation at 30° C. for 3 to 4 days to again form colonies and pouring a Congo Red dye solution to obtain colonies whose periphery was not dyed in contrast to the dyed red agar-agar. The colonies were collected from the master plate and high titer CMCase-producing bacilli was screened.

By the above procedure, Bacillus sp. KSM-635 (FERM BP 1485) was isolated.

(ii) The strain of Bacillus sp. KSM-635 (FERM BP 1485) was aerobically cultivated in a liquid medium consisting of 1.5% of meat extract, 0.5% of yeast extract, 1% of CMC, 0.1% of $KH_2PO_4$ and 0.755 of $Na_2CO_3$ at 34° C. for 2 days. 3 liters of cooled ethanol ($-10°$ C.) were gradually added to 1 liter of a supernatant liquid of the culture product to cause proteins to precipitate. The precipitate was dissolved in a minimum amount of sterilized deionized water and neutralized with diluted acetic acid, followed by dialysis with running water for 15 hours and freeze-drying to obtain 9.8 g of alkaline cellulase $K_2$ (2500 u/g).

Figure 1:
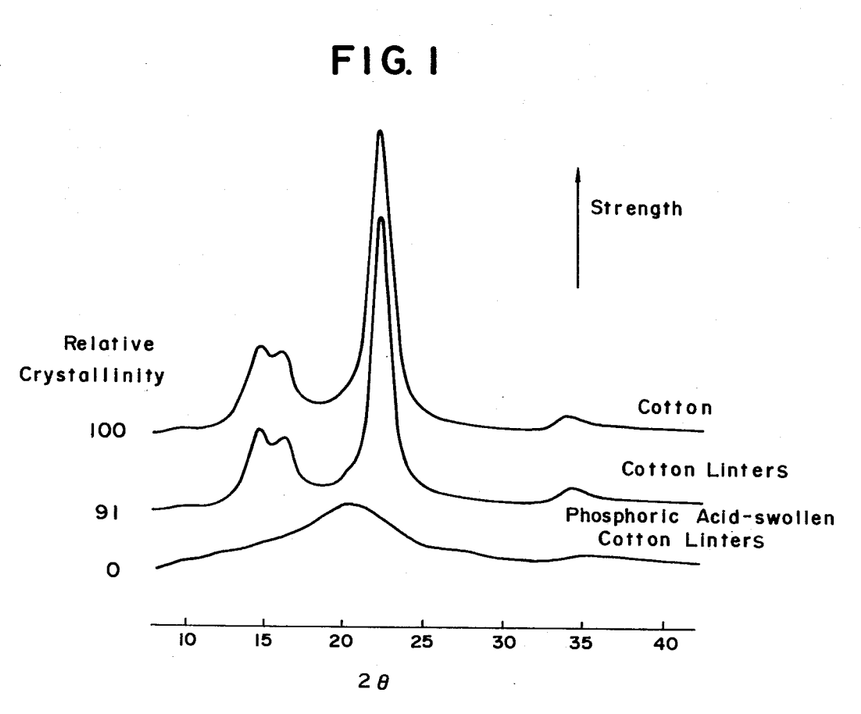
FIG. 1 is an X-ray diffraction pattern of cotton linters and phosphoric acid-swollen cotton linters used as a substrate for calculation of a non-degrading index.

(iii) The alkaline cellulase K obtained in (ii) was purified by affinity chromatography. Supports for the chromatography used were American raw cotton-derived cotton linters and phosphoric acid-swollen cotton linters. The X-ray diffraction patterns of these samples are shown in FIG. 1. Relative to the crystallinity of cotton (American raw cotton) and the phosphoric acid-swollen cotton linters is taken as 100% and 0%, respectively, the relative crystallinity was found to be 91%. The support used had a particle size of not larger than 53 micrometers. The respective supports were each charged into a column. Under conditions of a column capacity of 10 ml, a fraction size of 1.6 ml and a flow rate of 10 ml/hr, the column was first sufficiently washed with a 0.1 M phosphate buffer solution (pH 8.0), into which 12 ml of the buffer solution with 0.01 wt% of the cellulase. Thereafter, 25 ml of the above buffer solution and 8 ml of a 0.005 M phosphate buffer solution (pH 8.0) were passed, followed by finally washing the column with the buffer solution.

Figure 2:
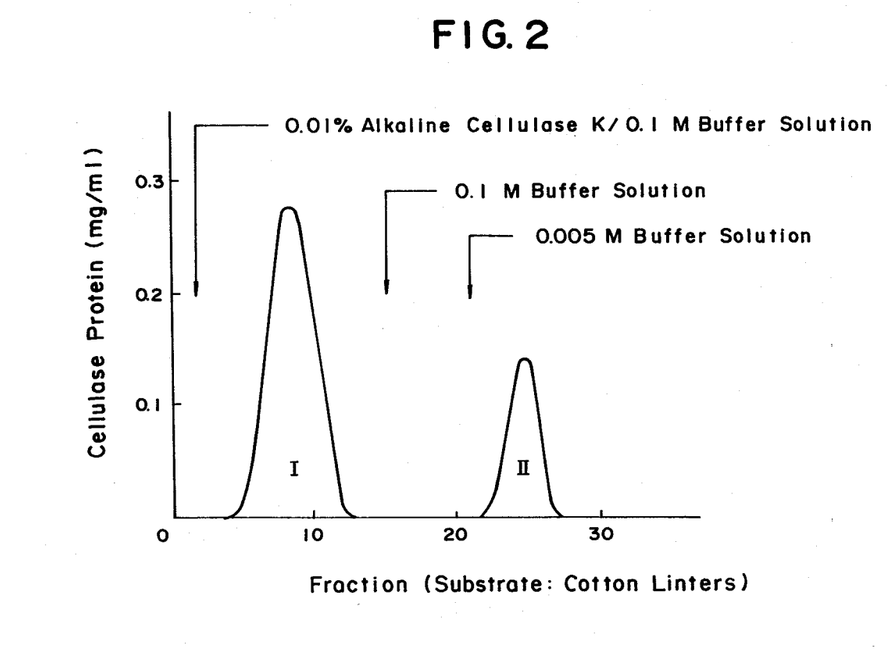
FIGS. 2 and 3 are, respectively, schematic affinity chromatograms showing the respective fractions of alkaline cellulase K.

When the cotton linters were used as the support, it had a non-adsorbed fraction I and an adsorbed fraction II as shown in FIG. 2.

Figure 3:
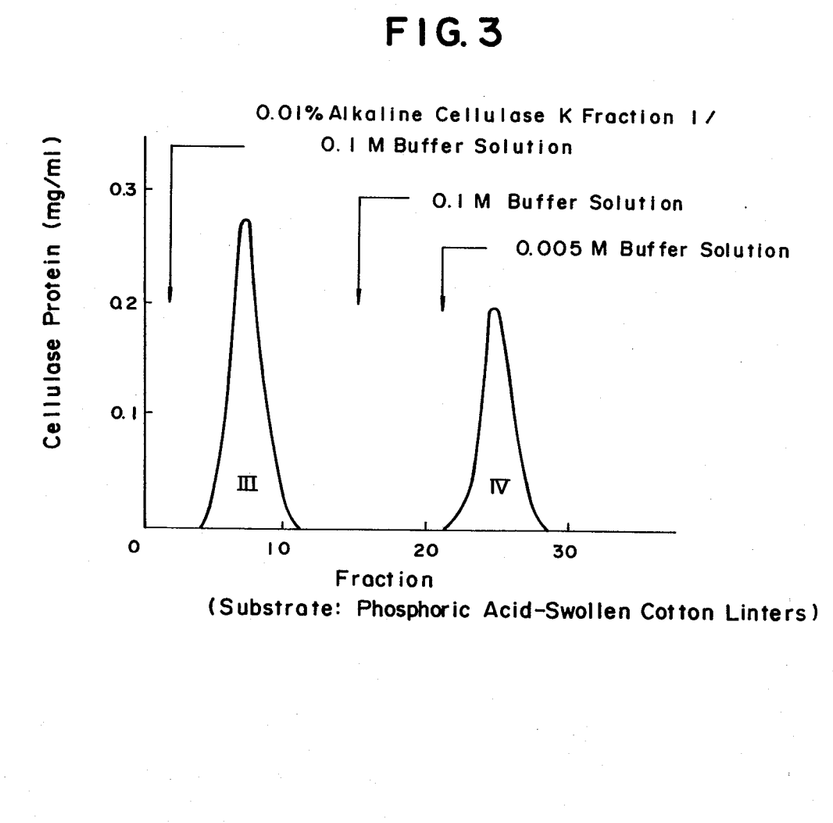

On the other hand, when the phosphoric acid-swollen cotton linters were used as the support and the non-adsorbed fraction I was similarly fractionated in the cotton linters, there were obtained, as shown in FIG. 3, a non-adsorbed fraction III and an adsorbed fraction IV in the phosphoric acid-swollen cotton linters.

It will be noted that because the fractions II, III and IV had, respectively, the CMC degrading activity, they were found to be all cellulase proteins.

(iv) Determination of non-degrading index

The index was determined according to the afore-described measuring method of non-degrading index. More particularly, cotton linters (highly crystalline cellulose) and phosphoric acid-swollen cotton linters (low-crystalline cellulose) were, respectively, provided as a substrate. While varying the concentration of the enzyme, an amount of reducing sugar was measured according to the PHBAH method to determine a hydrolytic rate in the linear region. Then, the non-degrading index was calculated according to the following equation. The results are shown in Table 4 below.

$$\text{Non-degrading index} = \frac{\text{hydrolytic rate for low-crystalline cellulose}}{\text{hydrolytic rate for highly-crystalline cellulose}}$$

TABLE 4

| Sample | Non-degrading Index |
| --- | --- |
| Alkaline cellulase K | 500 |
| Fraction II | 50 |
| Fraction III | 500 |
| Fraction IV | 600 |

Example 1

Detergents indicated in Table 5 were prepared to determine the detergency (dirt-removing action). The non-degrading property for cotton was also determined in terms of tensile strength. The results are shown in Table 6. The cellulase used was formulated in each detergent composition in an amount of 1000 U/kg as CMC activity. (Detergency measuring method)

(a) Preparation of soiled cloth (artificially contaminated cloth):

The Kanuma red earth soil for horiculture was dried at 120° C.±5° C. for 4 hours and sufficiently milled. A 150 mesh (100 micrometers) sieve-passing soil was dried at 120° C.±5° C. for 2 hours. 150 g of the soil was dispersed in 1 liter of perchloroethylene, which was contacted with a shirting #2023 cloth, followed by brushing to remove the dispersion and an excess of deposited dirt (Japanese Patent Application Laid-open No. 55-26473). 10 cm x 10 cm test pieces were made for tests.

(b) Washing conditions, washing method and evaluation

Each detergent was dissolved in 4°DH hard water to prepare 1 liter of a 0.133% detergent solution. Five test cloth pieces were added to the detergent aqueous solution and washed under agitation in a Targo-to-meter at 100 r.p.m. at 30° C. for 10 minutes. After rinsing with running water, the test pieces were iron pressed and subjected to the measurement of reflectance.

The original cloth prices prior to the washing and the contaminated cloth pieces prior to and after the washing were measured by means of an automatic recording colorimeter (Shimazu Seisakusho, Ltd.) with respect to reflectance at 460 nm and the washing rate (%) was calculated according to the following equation.

$$\text{Washing rate} = \frac{\text{reflectance after washing} - \text{reflectance prior to washing}}{\text{reflectance of original cloth} - \text{reflectance prior to washing}} \times 100$$

The results are shown as an average value of five measurement.

(c) Tensile strength test of cloth

100% cotton underwears were immersed for 120 minutes in each of the solutions which were obtained by dissolving 40 g of detergents, indicated in Table 6, in 5 liters of 3° DH water at 30° C. Thereafter, 25 liters of water of 30° C. and 3° DH were added, followed by washing for 10 minutes in a domestic full automatic washing machine. The underwears were dried and a similar immersing and washing procedure was repeated 100 times. The resultant dried articles were used for the tensile test.

The cotton underwears were cut into pieces with a size of 1 cm x 10 cm and subjected to measurement of tensile strength using a tensile tester, TEN-SILON UTM-III-100, (load cell 10 kg) made by Toyo Baldwin Co., Ltd.

TABLE 5

| Component | #A Powder Detergent | #B Liquid Detergent |
| --- | --- | --- |
| Linear sodium alkylbenzene sulphonate (LAS; C = 12) | 12 | — |
| Sodium alkylsulphate ($C_{16}$–$C_{18}$) (AS; C = 14) | 4 | — |
| Sodium alkylethoxy sulphate (AES; C = 12, EO = 2.5 mol) | — | 20 |
| Polyoxyethylenealkyl ether (AE; C = 12.5, EO = 7 mol) | 4 | 20 |
| Sodium hardened tallow fatty acid | 2 | — |
| Coconut oil fatty acid | — | 3 |
| Monoethanol amine | — | 5 |
| Ethanol | — | 7 |
| Polyethylene glycol (MW = 12000) | 2 | 2 |
| Sodium polyacrylate | 2 | — |

TABLE 5-continued

| Component | #A Powder Detergent | #B Liquid Detergent |
|---|---|---|
| (MW = 8000) | | |
| 4A-type Zeolite | 18 | — |
| Sodium silicate (JIS No. 2) | 10 | — |
| Sodium carboxylate | 10 | — |
| Glauber's salt | balance | — |
| Sodium sulfite (anhydride) | 1 | — |
| Protenase | 0.5 | 1 |
| Cellulase | 2 or 0 | 2 or 0 |
| Fluorescent whitening agent | 0.2 | 0.2 |
| Sodium succinic acid | — | 3 |
| Potassium chloride | — | 0.1 |
| Water | 4 | balance |
| Total | 100 | 100 |

TABLE 6

| | Detergent Composition | | | |
|---|---|---|---|---|
| | #A Powder Detergent | | #B Liquid Detergent | |
| Enzyme Fraction | Detergent Rate (%) | Tensile Strength (kg) | Detergent Rate (%) | Tensile Strength (kg) |
| nil (Standard Detergent) | 60.5 ± 0.6 | 7.2 ± 0.6 | 58.5 ± 0.3 | 7.3 ± 0.4 |
| II (Comparative Detergent) | 72.2 ± 0.5 | 5.8 ± 0.5 | 68.4 ± 0.5 | 5.9 ± 0.3 |
| III (Inventive Detergent) | 68.5 ± 0.5 | 7.2 ± 0.3 | 66.3 ± 0.3 | 7.2 ± 0.6 |
| IV (Inventive Detergent) | 73.0 ± 0.4 | 7.4 ± 0.7 | 69.5 ± 0.4 | 7.1 ± 0.5 |
| Alkaline Cellulase K (Present Invention) | 69.3 ± 0.5 | 7.1 ± 0.6 | 67.0 ± 0.5 | 7.1 ± 0.5 |

As will be apparent from the above results, the cellulase of the invention have not only good washing effects especially on dirt and soil, but also a low degrading effect on cotton, and when applied to clothing detergents, they have good practical utility.

With the fraction IV adsorbed on the phosphoric acid-swollen cotton linters and the non-adsorbing fraction III, a slight difference in the washing effect is found, i.e. the fraction IV has a better washing effect. However, both exhibit a good washing effect and cannot degrade cotton, so that they are useful as a cellulase for washing in practical application.

Example 2

Detergent compositions for clothing using the powder detergent composition of Example 1 and cellulases produced from various microorganisms were prepared. These compositions were subjected to the washing test and the tensile strength test in the same manner as in Example 1. The results are shown in Table 7.

TABLE 7

| Cellulase | Non-degrading Index | Detergent Rate (%) | Tensile Strength (kg) |
|---|---|---|---|
| Alkaline Cellulase K-521 | 800 | 71.5 ± 0.7 | 7.2 ± 0.4 |
| Alkaline Cellulase K-522 | 1000 | 70.7 ± 0.6 | 7.3 ± 0.5 |
| Alkaline Cellulase K-580 | 600 | 70.4 ± 0.4 | 7.2 ± 0.3 |
| Alkaline Cellulase K-534 | 600 | 70.2 ± 0.6 | 7.2 ± 0.5 |
| Alkaline Cellulase K-539 | 800 | 68.7 ± 0.4 | 7.3 ± 0.4 |
| Alkaline Cellulase K-577 | 800 | 69.4 ± 0.5 | 7.2 ± 0.5 |
| Alkaline Cellulase K-588 | 1000 | 68.5 ± 0.5 | 7.2 ± 0.4 |
| Alkaline Cellulase K-344 | 300 | 68.1 ± 0.6 | 6.2 ± 0.3 |
| Fraction IV of Alkaline Cellulase K-344 | 600 | 69.0 ± 0.5 | 7.1 ± 0.3 |
| Alkaline Cellulase K-425 | 350 | 68.7 ± 0.4 | 6.3 ± 0.3 |
| Fraction IV of Alkaline Cellulase K-425 | 600 | 69.4 ± 0.5 | 7.2 ± 0.5 |
| Cellzyme 2400T | 10 | 68.0 ± 0.7 | 4.9 ± 0.6 |

Example 3

| | |
|---|---|
| Sodium linear dodecylbenzenesulfonate | 14 (wt %) |
| Polyoxyethylene alkyl ether ($C_{12-13}$: EO 10 moles) | 6 |
| Hardened sodium tallow fatty acid | 2 |
| No. 2 sodium silicate | 10 |
| Sodium carbonate | 25 |
| 4A-type zeolite | 25 |
| Sodium sulfate | balance |
| Sodium sulfite | 1 |
| Polyethylene glycol (molecular weight 6000) | 2 |
| Cellulase (IV fraction of Example 1) | 2 |
| Water | 4 |

Example 4

| | |
|---|---|
| Sodium linear dodecylbenzenesulfonate | 10 (wt %) |
| Sodium dodecylsulfate | 2 |
| Polyoxyethylene alkyl ether ($C_{12-13}$: EO 7.7 moles) | 8 |
| Hardened sodium tallow fatty acid | 2 |
| No. 1 sodium silicate | 10 |
| Sodium carbonate | 20 |
| 4A-type zeolite | 25 |
| Sodium pyrophosphate | 15 |
| Sodium sulfate | balance |
| Polyethylene glycol (molecular weight 11000) | 1 |
| Sodium sulfite | 1 |
| Alkaline cellulase K-521 | 2 |
| Water | 4 |

Example 5

| | |
|---|---|
| Polyoxyethylene alkyl ether (R: tallow alcohol, EO: 8.6 moles) | 20 (wt %) |
| Hardened sodium tallow fatty acid | 2 |
| Sodium tripolyphosphate | 30 |
| Sodium perborate | 20 |
| No. 2 sodium silicate | 10 |
| Sodium carbonate | 5 |
| Sodium sulfite | 1 |
| Polyethylene glycol (molecular weight 6000) | 2 |
| Alkaline cellulase K-580 | 2 |
| Water | 6 |
| Sodium sulfate | balance |

The clothing detergent compositions of Examples 3 to 5 were compared with a cellulase-free comparative composition with respect to the detergency and fiber strength. As a result, it was found that the detergency was significantly higher for the cellulase-containing systems with no recognized difference in the fiber strength.

What is claimed is:

1. A detergent composition for clothing which comprises at least one surface active agent and an amount of from 50 to 20,000 units, per kg of the detergent composition, in terms of an enzymatic activity determined when carboxymethyl cellulose (CMC) is used as a substrate of a cellulase
  selected from the group consisting of alkaline cellulase K, alkaline cellulase K-344, alkaline cellulase K-534, alkaline cellulase K-539, alkaline cellulase K577, alkaline cellulase K-425, alkaline cellulase K-521, alkaline cellulase K-580, alkaline cellulase K-588, alkaline cellulase K-597, alkaline cellulase K-522, CMCase I, CMCase II, alkaline cellulase E-Ii and alkaline cellulase E-III.

* * * * *